United States Patent [19]
Foley et al.

[11] Patent Number: 5,936,730
[45] Date of Patent: Aug. 10, 1999

[54] BIO-MOLECULE ANALYZER WITH DETECTOR ARRAY AND FILTER DEVICE

[75] Inventors: Barbara M. Foley; Wenbin Jiang, both of Phoenix; Davis H. Hartman, Chandler; Huinan Yu, Phoenix; Sean Gallagher, Scottsdale, all of Ariz.

[73] Assignee: Motorola, Inc., Schaumburg, Ill.

[21] Appl. No.: 09/149,507

[22] Filed: Sep. 8, 1998

[51] Int. Cl.[6] ............ G01N 21/00; G01N 21/01; G01N 27/02; G01B 9/02
[52] U.S. Cl. ............ 356/344; 356/346; 356/244; 356/73; 356/327; 356/365; 422/82.02
[58] Field of Search .................... 356/344, 346, 356/244, 73, 327, 365, 39; 422/82.02

[56] References Cited

U.S. PATENT DOCUMENTS

| | | | |
|---|---|---|---|
| 5,500,188 | 3/1996 | Hafeman et al. | 422/82.02 |
| 5,543,018 | 8/1996 | Stevens et al. | 356/344 |
| 5,710,628 | 1/1998 | Waterhouse et al. | 356/344 |
| 5,736,410 | 4/1998 | Zarling et al. | 356/346 |

*Primary Examiner*—Frank G. Font
*Assistant Examiner*—Roy M. Punnoose
*Attorney, Agent, or Firm*—Eugene A. Parsons; William E. Koch

[57] ABSTRACT

A bio-molecule analyzer including a plurality of test sites on a transparent substrate, each test site having probe molecules attached thereto. An array of addressable light sources are positioned in optical alignment with a corresponding test site. A solution containing sample molecules is positioned in contact with the plurality of test sites. A detector array having a plurality of photodetectors positioned in optical alignment with the array of addressable light sources, one photodetector corresponding to each light source, and a light filter positioned between the detector array and the plurality of test sites for absorbing the light from the light sources and transmitting the light from the test sites to the detector array.

20 Claims, 1 Drawing Sheet

BIO-MOLECULE ANALYZER WITH DETECTOR ARRAY AND FILTER DEVICE

FIELD OF THE INVENTION

This invention relates to analysis of molecular samples.

More particularly, the present invention relates novel analyzers and methods of analyzing bio-molecule samples.

BACKGROUND OF THE INVENTION

Identification of molecular structure has become very important in many industries. In particular, biological molecules such as nucleic acids and proteins are analyzed to form the basis of clinical diagnostic assays. The procedures utilized often involve large numbers of repetitive steps which consume large amounts of time. With the advent of large projects such as the human genome project, faster and less complex techniques are required.

Simpler and quicker analysis of molecules has been provided by the development of devices often referred to as bio chips, which are arrays of test sites formed on a substrate. Each of the plurality of test sites includes probes therein to bond with target molecules from samples applied to the device. The binding of a molecule to a probe is noted, thereby identifying the molecule.

Once fabrication of an analyzer having an array of test sites has been completed, a method for the detection of the bonding of the probe with a target molecule must be provided. There are many techniques for determining which test sites have molecules bonded to them including autoradiography, optical detection (fluorescence) and electronic detection. As the number of test sites in an array is increased, the complexity of detecting the bonding event is also increased. Therefore, improving methods of detection, specifically optical detection, are required.

It would be highly advantageous, therefore, to remedy the foregoing and other deficiencies inherent in the prior art.

Accordingly, it is an object of the present invention to provide a new and improved apparatus and method for analyzing molecules.

Another object of the present invention is to provide a method and apparatus for analyzing molecules using optical detection.

And another object of the present invention is to provide a method and apparatus for optically analyzing molecules which has aligned light sources and detectors.

A further object of the present invention is to provide a method and apparatus for analyzing molecules wherein the light source array used to fabricate the test sites, and is therefore self aligned with the test sites, is used as the excitation source in optical detection without interfering with the detection.

SUMMARY OF THE INVENTION

Briefly, to achieve the desired objects of the instant invention, in accordance with a preferred embodiment thereof, provided is a bio-molecule analyzer including a plurality of test sites on a transparent substrate, each test site having probe molecules attached thereto. An array of addressable light sources are positioned in optical alignment with a corresponding test site. A solution containing sample molecules is positioned in contact with the plurality of test sites. A detector array having a plurality of photodetectors positioned in optical alignment with the array of addressable light sources, one photodetector corresponding to each light source, and a light filter positioned between the detector array and the plurality of test sites for absorbing the light from the light sources and transmitting the light from the test sites to the detector array.

In specific embodiments, a bio-molecule analyzer has an array of light sources which include either an array of light emitting diodes or an array of vertical cavity surface emitting lasers. Furthermore, in specific embodiments, the filter device of the bio-molecule analyzer include either a wavelength filter or a polarizer.

Also provided is a method of analyzing a sample solution containing sample molecules. The method includes providing an integrated bio-molecular-array including a transparent substrate carrying a plurality of test sites on a first surface, each test site having probe molecules attached thereto, and an array of addressable light sources carried by an opposing second surface of the transparent substrate, each addressable light source being in optical alignment with a corresponding test site of the plurality of test sites and emitting a first light. The sample solution containing sample molecules is positioned in contact with the plurality of test sites so that the sample molecules bond with specific probe molecules. The bonded sample and probe molecules fluoresce a second light when excited by the first light. The sample solution is removed, and the bonded sample and probe molecules are excited with the first light from the array of addressable light sources. The second light from the fluorescing of the bonded sample and probe molecules are detected.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENTS

Figure 1:
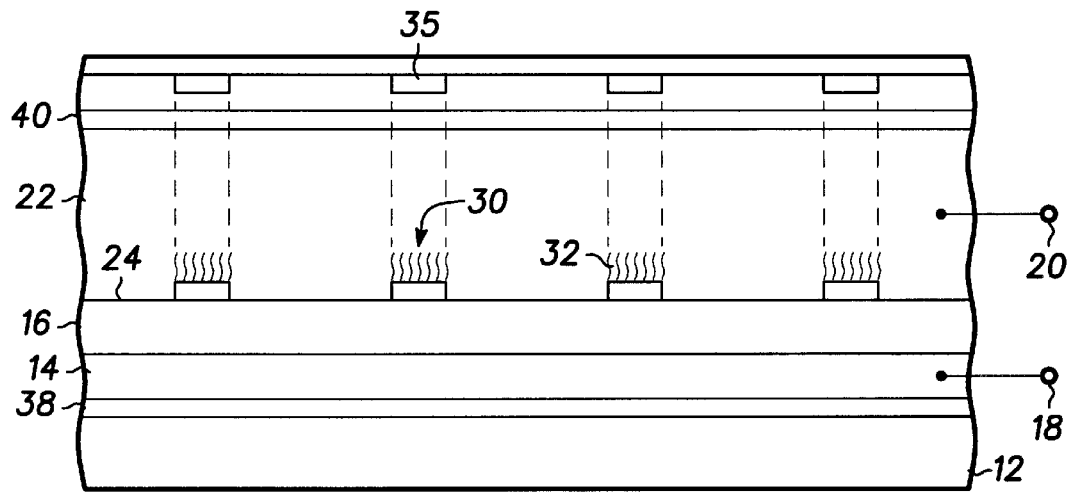
FIG. 1 is a sectional view of a bio-molecule analyzer according to the present invention.

Turning now to the drawings in which like reference characters indicate corresponding elements throughout the several views, attention is first directed to FIG. 1 which illustrates a bio-molecule analyzer generally designated 10. Bio-molecule analyzer 10 includes a substrate 12 preferably fabricated of silicon, glass, plastic, etc., a thin conductive layer 14 formed on substrate 12, and a photoconductive layer 16 formed on thin conductive layer 14. Thin conductive layer 14 can be any conductive material such as gold, platinum etc., and can be indium tin oxide (ITO) or other optically transparent conductors for reasons which will become apparent from the subsequent description. Photoconductive layer 16 is a material such as amorphous silicon, CdS, CdSe, various photoconductive polymers, etc. which becomes conductive when subjected to light.

Still referring to FIG. 1, during the fabrication of analyzer 10, a lead 18 is coupled to conductive layer 14 and a lead 20 is coupled to a solution (not shown) positioned in electrical contact with a surface 24 of photoconductive layer 16 opposite to conductive layer 14. While not specifically shown, it will be understood that the solution is in electrical contact only with surface 24 and not with conductive layer 14. A potential is applied across leads 18 and 20 and thus between the solution and conductive layer 14 to attract probe molecules to test sites in the fabrication of analyzer 10 as will be described presently. For more details of the fabrication process see co-pending U.S. Patent Application filed of even date herewith, entitled "Bio-Molecule Analyzer with Photosensitive Material and Fabrication", attorney docket number CR98-009.

Briefly, in the fabrication of analyzer 10 and still referring to FIG. 1, an array of light sources 31 directs beams of light 33 through portions 34 of photoconductive layer 16 defining test sites 30 (preferably one test site for each beam). In this embodiment, test sites 30 are formed into an array, with each test site 30 being an area of surface 24 substantially coextensive with a corresponding portion 34. Beams of light 33 complete an electrical circuit between conductive layer 14 and the solution through each portion 34 of photoconductive layer 16. This is accomplished by a beam (or beams) of light 33 temporarily converting a portion (or portions) 34 of photoconductive layer 16 to a conducting medium.

The solution contains ionic probe molecules to be bound to test sites 30. By completing the circuit, the ionic probe molecules in the solution are attracted to and concentrate proximate surface 24 at a selected one or ones of test sites 30. It will be understood that any method of controllably illuminating a selected portion 34 of photoconductive layer 16 can be used, such as a masked light source, the use of a laser or diode array 31 or similar device instead of or in combination with a mask which permits passage of light in only the desired locations. The array can be a one dimensional or two dimensional array of light sources 31 which are individually addressable, i.e. one or more light sources 31 can be activated as desired.

As illustrated in FIG. 1 the array of test sites 30 (microlocations) defined on surface 24 have groups of probes 32 coupled thereto. Each test site 30 contains a plurality of probes 32 which are capable of binding to specific molecular structures. The molecular structure can comprise, for example, biopolymers such as polynucleotides, protein, DNA, RNA, cells, enzymes, antibodies, antigens, etc. In the case of DNA or RNA testing, probes 32 can comprise, for example, oligonucleotides. All probes 32 at a given test site 30 are identical. Probes in respective test sites differ in sequence for simultaneous detection of a plurality of different target molecules within a single array. Each test site 30 is individually addressable by array of light sources 31 to provide the ability to attract ionic probe molecules from the solution to selected test site(s) 30 in order to fabricate an array of test sites each for detecting different molecules or sequences.

By incorporating the array of light sources 31 directly with analyzer 10, processing is simplified, and array of light sources 31 is used to both facilitate bonding of probe molecules to specific test sites, and also since the beam of light defines the test site, it is self aligned for use as a light source for the excitation beam in optical detection.

To analyze a sample using analyzer 10 of FIG. 1, a solution 22 containing the sample bio-molecules is introduced into analyzer 10. Solution 22 is positioned in contact with the plurality of probe molecules 32 at each of the plurality of test sites 30 so as to allow interaction between the sample bio-molecules and the pluralities of probe molecules. Solution 22 is removed and the array of light sources 31 is employed as excitation sources for optical detection of the binding events between the sample molecules and the corresponding probe molecules, i.e. hybridization, etc. Thus, the interaction between matching sample bio-molecules and probe molecules is easily detected.

Typically, sample molecules have fluorophores (fluorescent tags) attached thereto, which fluoresce when excited by a light source. To detect the fluorescent emissions from the bonded sample molecules, each detector 35 of an array of detectors is optically aligned with light sources 31 with test sites 30 therebetween. In this embodiment, array of detectors 35 is constructed with dimensions similar to the dimensions of the array of light sources 31. Alignment of detectors 35 and light sources 31 can be accomplished in numerous conventional manners such as by a photolithographic pattern of offsets. Since detectors 35 are aligned with light sources 31 light beams 33 not only excite fluorescent tags on bonded sample molecules, but also impinge directly on detectors 35, overwhelming the fluorescence. In this specific embodiment, light sources 31 emit polarized light, as for example from lasers (e.g. VCSEL, edge emitting lasers, etc.). To prevent light beams from overwhelming detectors 35, a light filter 40 is positioned between detectors 35 and test sites 30 for absorbing ( i.e. preventing transmission, which can include absorbing, blocking, deflecting etc. hereinafter referred to as 'absorbing') the light emitted from light sources 31 and transmitting light emitted from the fluorescence of the excited fluorescent tags.

In the present embodiment, to prevent transmission of the light generated from light sources 31 and to transmit light generated by fluorescence, light filter 40 is, for example, either a polarizing filter or a wavelength filter. Light beams 33 are polarized since they are emitted from a polarized light source such as lasers. Thus, to prevent interference with detectors 35, light beams 33 are absorbed by a polarizing filter (light filter 40) set perpendicular to the polarization thereof. The light from the fluorescence is unpolarized, therefore substantially 50 percent is transmitted to detectors 35. Alternatively, if the wavelength of light beams 33 does not overlap significantly with the wavelength of light generated by fluorescence then light filter 40 can be a wavelength filter.

Figure 2:
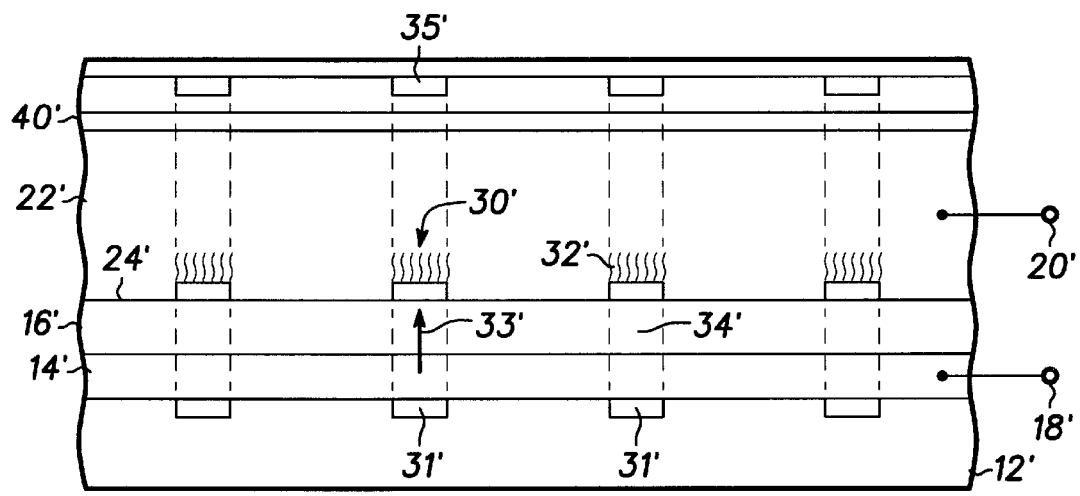
FIG. 2 is a sectional view illustrating another embodiment of a bio-molecule analyzer according to the present invention.

Turning now to FIG. 2, another embodiment of an analyzer generally designated 10' is illustrated wherein similar elements are designated with similar numbers having a prime added to indicate the different embodiment. A complete discussion of elements previously described is omitted for purposes of simplicity, with descriptions focusing on the differences between the embodiments. In this specific embodiment, light sources 31' emit unpolarized light, as for example from light emitting diodes (e.g. OEL, LED, etc.). To prevent light beams from overwhelming detectors 35', a light filter 40' is positioned between detectors 35' and test sites 30' for absorbing the light emitted from light sources 31' and transmitting light emitted from the fluorescence of the excited fluorescent tags.

In the present embodiment, to prevent transmission of the light generated from light sources 31' and to transmit light generated by fluorescence, light filter 40' is, a wavelength filter. The wavelength of light beams 33' does not overlap significantly with the wavelength of light generated by fluorescence. Thus, light filter 40 is a wavelength filter specific to the wavelength of light emitted by light sources 31'.

Figure 3:
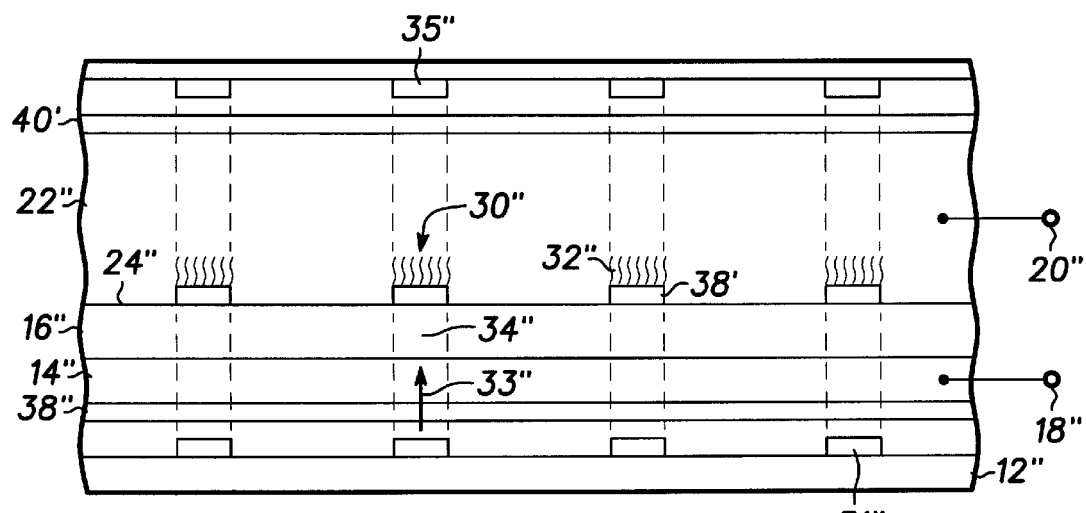
FIG. 3 is a sectional view illustrating yet another embodiment of a bio-molecule analyzer according to the present invention.

Turning now to FIG. 3, yet another embodiment of an analyzer generally designated 10" is illustrated wherein similar elements are designated with similar numbers having a double prime added to indicate the different embodiment. A complete discussion of elements previously described is omitted for purposes of simplicity, with descriptions focusing on the differences between the embodiments. In this specific embodiment, light sources 31" emit unpolarized light, as for example from light emitting devices (e.g. organic electroluminescent devices, semiconductor light emitting diodes, etc.). In this embodiment, a polarizer 38" is positioned between the array of light sources 31" and thin conductive layer 14" to polarize the light emitted from light sources 31". However, it should be understood that polarizer 38" can be positioned anywhere between light sources 31" and test sites 30".

To prevent light beams from overwhelming detectors 35", a light filter 40" is positioned between detectors 35" and test sites 30" for absorbing the polarized light emitted from light sources 31" and transmitting light emitted from the fluorescence of the excited fluorescent tags.

In the present embodiment, to prevent transmission of the light generated from light sources 31" and to transmit light generated by fluorescence, the light filter is a polarizing filter 40". Thus, to prevent interference with detectors 35", unpolarized light emitted by light sources 31" is polarized by polarizer 38" to produce polarized light beams 33" which provide the excitation energy for fluorescence and are subsequently absorbed by polarizing filter 40" set perpendicular to the polarization of light beams 33". The light from the fluorescence is unpolarized, therefore substantially 50 percent is transmitted to detectors 35".

Thus, provided is a new and improved apparatus and method for analyzing molecules by optical detection using aligned light sources and detectors. The light source array which is used to fabricate the test sites, is therefore self aligned with the test sites, and is used as the excitation source in optical detection in conjunction with light filters to prevent interference with the detection. The light filters can be conveniently integrated with the light detectors and the light sources can be polarized by integrated polarizers when needed.

Various modifications and changes to the embodiments herein chosen for purposes of illustration will readily occur to those skilled in the art. Other modifications and variations may be made by those skilled in the art without departing from the scope of the invention as defined by the following claims.

Having fully described and disclosed the present invention and preferred embodiments thereof in such clear and concise terms as to enable those skilled in the art to understand and practice same, the invention claimed is:

1. A bio-molecule analyzer comprising:
   a transparent substrate carrying a plurality of test sites on a first surface each test site having probe molecules attached thereto and characterized as bonding with a plurality of sample molecules dependent upon molecular structure;
   an array of addressable light sources adjacent an opposing second surface of the transparent substrate, each addressable light source being in optical alignment with a corresponding test site of the plurality of test sites and emitting light of a first wavelength;
   means for receiving a solution containing the plurality of sample molecules in contact with the plurality of test sites, the plurality of sample molecules characterized as reactive to the light of a first wavelength so as to fluoresce when excited by the light of a first wavelength and transform a portion of the light of a first wavelength into light of a second wavelength;
   a detector array having a plurality of photodetectors positioned in spaced relation with the first surface of the transparent substrate and said plurality of test sites and in optical alignment with the array of addressable light sources, one photodetector corresponding to each light source; and
   a light filter positioned between the detector array and the plurality of test sites for absorbing the light of a first wavelength and transmitting therethrough the light of a second wavelength to the detector array.

2. A bio-molecule analyzer as claimed in claim 1 wherein the array of light sources includes one of an array of light emitting diodes and an array of vertical cavity surface emitting lasers.

3. A bio-molecule analyzer as claimed in claim 1 wherein the filter device includes a wavelength filter.

4. A bio-molecule analyzer as claimed in claim 1 wherein the filter device includes a polarizer with a light polarity.

5. A bio-molecule analyzer as claimed in claim 1 wherein the light of a first wavelength is polarized and the filter device includes a polarizer with a light polarity orthogonal to the light of a first wavelength.

6. A bio-molecule analyzer as claimed in claim 4 wherein the array of light sources includes vertical cavity surface emitting lasers emitting the light of a first wavelength having a polarity orthogonal to the light polarity of the polarizer.

7. A bio-molecule analyzer as claimed in claim 4 wherein the array of light sources includes light emitting diodes and a light source polarizer emitting the light of a first wavelength having polarity orthogonal to the light polarity of the polarizer.

8. A bio-molecule analyzer comprising:
   an integrated bio-molecular-array including a transparent substrate carrying a plurality of test sites on a first surface each test site having probe molecules attached thereto and an array of addressable light sources carried by an opposing second surface of the transparent substrate, each addressable light source being in optical alignment with a corresponding test site of the plurality of test sites and emitting a light of a first wavelength;
   means for receiving a solution containing sample molecules in contact with the plurality of test sites, the sample molecules being bondable to specific probe molecules and fluorescing when excited by the light of a first wavelength to emit a light of a second wavelength;
   a detector array having a plurality of photodetectors positioned in spaced relation with the first surface of the transparent substrate and said plurality of test sites in optical alignment with the array of addressable light sources for detecting the light of a second wavelength, one photodetector corresponding to each light source; and
   a light filter positioned between the detector array and the plurality of test sites for absorbing the light of a first wavelength and transmitting the light of the second wavelength to the detector array.

9. A bio-molecule analyzer as claimed in claim 8 wherein the filter device includes a wavelength filter.

10. A bio-molecule analyzer as claimed in claim 8 wherein the filter device includes a polarizer with a light polarity.

11. A bio-molecule analyzer as claimed in claim 10 wherein the array of light sources includes vertical cavity surface emitting laser emitting the light of a first wavelength having polarity orthogonal to the light polarity of the polarizer.

12. A bio-molecule analyzer as claimed in claim 10 wherein the array of light sources includes light emitting diodes and a light source polarizer emitting the light of the first wavelength having a polarity orthogonal to the light polarity of the polarizer.

13. A method of analyzing a sample solution containing sample molecules, comprising the steps of:

provided an integrated bio-molecular-array including a transparent substrate carrying a plurality of test sites on a first surface, each test site having probe molecules attached thereto, and an array of addressable light sources carried by an opposing second surface of the transparent substrate, each addressable light source being in optical alignment with a corresponding test site of the plurality of test sites and emitting a light of a first wavelength;

positioning the sample solution containing sample molecules in contact with the plurality of test sites so that the sample molecules bond with specific probe molecules, bonded sample and probe molecules fluorescing a light of a second wavelength when excited by the light of a first wavelength;

removing the sample solution;

exciting the bonded sample and probe molecules with the light of a first wavelength from the array of addressable light sources, and detecting the light of a second wavelength from the fluorescing of the bonded sample and probe molecules.

14. A method as claimed in claim 13 wherein the step of detecting the light of a second wavelength from the fluorescing of the bonded sample and probe molecules includes a step of filtering to remove the light of a first wavelength and transmit the light of a second wavelength.

15. A method as claimed in claim 14 wherein the step of detecting further includes the step of providing an array of photodetectors each aligned with a corresponding light source of the array of light sources.

16. A method as claimed in claim 15 wherein the step of filtering includes providing a filter device positioned between the array of photodetectors and the plurality of test sites.

17. A method as claimed in claim 16 wherein the filter device includes a wavelength filter.

18. A method as claimed in claim 16 wherein the filter device includes a polarizer with a light polarity.

19. A method as claimed in claim 14 wherein the array of light sources includes vertical cavity surface emitting laser emitting the light of a first wavelength having a polarity orthogonal to the light polarity of the polarizer.

20. A method as claimed in claim 18 wherein the array of light sources includes light emitting diodes and a light source polarizer emitting the light of a first wavelength having a polarity orthogonal to the light polarity of the polarizer.

* * * * *